United States Patent [19]
Loeffler

[11] 3,935,170
[45] Jan. 27, 1976

[54] TRIVALENT ANTIMONY CATALYST

[75] Inventor: Otto Ernest Loeffler, Rahway, N.J.

[73] Assignee: NL Industries, Inc., New York, N.Y.

[22] Filed: Feb. 3, 1975

[21] Appl. No.: 546,794

Related U.S. Application Data

[62] Division of Ser. No. 391,121, Aug. 24, 1973, Pat. No. 3,899,522.

[52] U.S. Cl................................................. 260/75 R
[51] Int. Cl.².............................................. C08G 63/14
[58] Field of Search........................... 260/446, 75 R

[56] References Cited
UNITED STATES PATENTS
3,484,410   12/1969   Lazarus............................. 260/446

*Primary Examiner*—Paul R. Michl

[57] ABSTRACT

A novel antimony catalyst for polyester condensation reactions is described comprising trivalent antimony having its valences occupied by dianion radicals of 1,2-diols and anion radicals or organic carboxylic acids. The molar ratio of antimony to dianion radical of 1,2-diol to anion radical of organic carboxylic acid is 1:1:1. The antimony compound is prepared by reacting a mixture of a 1,2-diol and a trivalent antimony reactant represented by the formula;

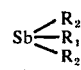

wherein Sb is antimony, $R_1$ is an anion radical of an organic carboxylic acid; and $R_2$ is selected from the group consisting of anions of alcohols, anions of organic carboxylic acids and mixtures thereof.

1 Claim, No Drawings

TRIVALENT ANTIMONY CATALYST

This is a division of application Ser. No. 391,121, filed Aug. 24, 1973, now U.S. Pat. No. 3,899,522.

BACKGROUND OF THE INVENTION

This invention is concerned with a novel trivalent antimony compound useful as a catalyst in the manufacture of polyesters such as polyethylene terepthalate from dimethyl terepthalate and ethylene glycol. In addition, this invention is also concerned with a novel process for the preparation of said trivalent antimony catalyst.

In the past, many trivalent and pentavalent antimony compounds have been used as catalysts in the production of polyesters such as polyethylene terepthalate. Among these antimony compounds are antimony trioxide, antimony pentoxide, alkyl antimony compounds, aryl antimony compounds and the like. In fact, almost any compound containing antimony can be used as a catalyst for these polyesters. In choosing an antimony catalyst for the commercial production of polyethylene terepthalate however, consideration of cost of the catalyst and the amount of soluble antimony present in the polymerization medium are important factors.

In the commercial manufacture of polyethylene terepthalate usually a mixture of a diester of terephthalic acid such as dimethyl terepthalate and excess ethylene glycol is formed in the presence of a catalyst such as $Zn(OAc)_2 \cdot 2H_2O$. The mixture is heated to remove an alcohol from the diester with the formation of an ester-exchange product, diglycol terepthalate. An antimony catalyst, such as those mentioned above is then added to the reaction mixture, and the temperature is raised to from 250° to 300°C under reduced pressure to effect polycondensation and form the polyethylene terepthalate.

The amount of soluble antimony provided by the catalyst is an important criterion for judging an effective antimony catalyst. It is often desirable to utilize an antimony catalyst which provides a high degree of soluble antimony in the ethylene glycol reaction medium. This high antimony solubility aids in the activity of the catalyst which in turn causes the reaction to proceed at a faster rate. For example, antimony trioxide which is a frequently used catalyst for the production of polyethylene terepthalate is relatively inexpensive but provides very low antimony solubility in the ethylene glycol reaction medium. Antimony glycoloxide, $Sb_2(OCH_2CH_2O)_3$, another widely used catalyst, is relatively expensive and provides from only 1.5% to 1.7% soluble antimony at 80°C. The antimony catalyst of this invention, however, provides from 5.1% to 5.6% soluble antimony at 80°C which is marked improvement over the prior art catalysts mentioned above making it particularly desirable for commercial production of polyethylene terepthalate. The antimony catalyst of this invention can be produced cheaply by virtue of simple processing steps involving short reaction times and inexpensive starting materials.

It is an object of this invention to describe a novel antimony catalyst for the production of polyethylene terepthalate which provides a high degree of soluble antimony in the polyethylene terepthalate reaction medium.

A still further object is to describe a novel and inexpensive process for the production of said trivalent antimony catalyst.

SUMMARY OF THE INVENTION

The trivalent antimony compound of this invention comprises a mixed antimony 1,2diolate and carboxylate wherein the valences of antimony are occupied by dianion radicals of 1,2-diols and carboxylate anion radicals. The molar ratio of antimony to diol dianion radical to carboxylate anion radical is 1:1:1. The term 1,2-diol as used herein is meant to describe an organic dihydroxy compound wherein the hydroxyl groups are bonded to adjacent carbon atoms.

Although the structural formula is not known accurately, the X-ray diffraction pattern, infra-red absorption spectra and elemental analysis have been used to supplement the characterization of these compounds.

Some of the possible chemical structures which may describe the antimony catalyst based on spectral data and elemental analysis, are represented by the following formulae:

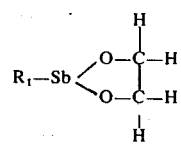

Formula 1

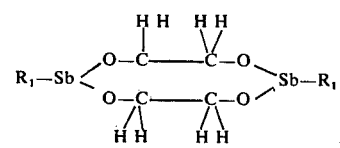

Formula 2

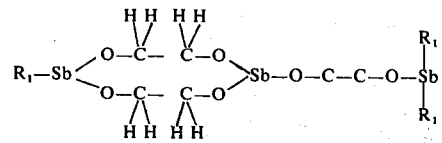

Formula 3

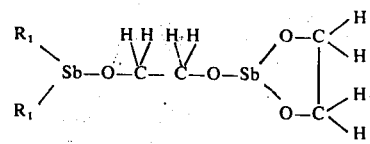

Formula 4 wherein $R_1$ is an anion radical of an organic carboxylic acid. The 1,2-diol dianion portion is represented by the formula $-[-O-CH_2-CH_2-O-]-$ which is the dianion radical of ethylene glycol. In all formulae shown above the ratio of antimony to 1,2-diol dianion radical to carboxylate anion radical is 1:1:1.

An example of a typical antimony compound is a mixed trivalent antimony ethylene glycoloxide and acetate; wherein

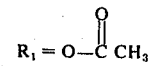

and the 1,2-diol portion is ethylene glycol dianion radical, $-[O-CH_2-CH_2-O]-$.

This antimony compound exhibits and X-ray diffraction pattern with characterizing d-spacings in the vicinity of 11.01, 5.43, 6.27 and 3.60A and has major infrared absorption peaks as 1720, 1375 and 1570 reciprocal centimeters. The compound has the following elemental analysis; about 16.8± 1 weight percent carbon; about 3.2± .4% weight percent hydrogen and about 50.3± weight percent antimony. These percentages correspond approximately to an emperical formula of $[C_4H_7O_4Sb]$.

The trivalent antimony compound is produced by a novel process comprising the steps of;

a. reacting a mixture of equimolar ratios of a 1,2-diol and a trivalent antimony reactant represented by the formula;

wherein Sb is antimony, $R_1$ is an anion radical of an organic carboxylic acid; and $R_2$ is selected from the group consisting of anions of alcohols, anions of organic carboxylic acids and mixtures thereof; and b. recovering a trivalent antimony compound from said mixture.

Among the typical antimony starting materials are antimony triacetate, antimony tributyrate, and antimony dibutoxide monoacetate. Typical 1,2-diols include ethylene glycol, 1,2-propane diol, 3-chloro-1,2-propane diol and mixtures thereof.

The reaction mixture should preferably contain a solvent to aid the fluidity of the mixture and the recovery of the formed trivalent antimony catalyst. Such solvents must be inert to the antimony reactant and the formed trivalent antimony compound and be capable of dissolving the 1,2-diol and the antimony starting material. Among such solvents include alcohols such as methyl alcohol, ethyl alcohol, propyl alcohol, isopropyl alcohol and butyl alcohol; ketonic solvents such as acetone, methyl ethyl ketone, diethyl ketone, methyl propyl ketone; and ethers such as diethylether, dipropyl ether, ethyl propyl, ether, dioxane and the like.

It the novel trivalent antimony compound, wherein the 1,2-diol dianion portion is ethylene glycol dianion is treated with excess ethylene glycol at high temperatures, antimony glycoloxide is formed. This constitutes a novel process for preparing said antimony glycoloxide and is also part of this invention.

DESCRIPTION OF THE PREFERRED EMBODIMENTS

The X-ray diffraction data, infra-red spectral data and elemental analysis for a trivalent antimony compound of this invention wherein $R_2=O_2C-CH_3$ and the 1,2-diol is ethylene glycol are repeated again in Table 1 below together with the preferred trivalent antimony reactant antimony triacetate, and for antimony glycoloxide which is a possible produce in the reaction of antimony triacetate with molar excesses of ethylene glycol at elevated temperatures as described in my copending U.S. Application Ser. No. 391,122 now U.S. Pat. No. 3,833,630.

TABLE 1

| | X-RAY DIFFRACTION (MAJOR d-Spacings) | INFRA-RED (Major Peaks) | | Elemental Analysis (weight percent) | |
|---|---|---|---|---|---|
| | | | | Calculated | Theoretical |
| Antimony Triacetate | Amorphous | 1720 | $cm^{-1}$ | | C=24.06 |
| | | 1637 | $cm^{-1}$ | | H= 3.01 |
| | | 1338 | $cm^{-1}$ | Sb=40.5 | Sb=40.70 |
| Antimony Glyoloxide | 3.22 A° | 1630 | $cm^{-1}$ | C=17.50 | C=17.03 |
| | 6.47 A° | 1450 | $cm^{-1}$ | H= 3.50 | H= 2.84 |
| | 6.35 A° | 1200 | $cm^{-1}$ | Sb=58.5 | Sb=57.6 |
| | 7.50 A° | | | | |
| Trivalent Antimony Compound ($R_1=CH_3$) | 11.01 A° | 1720 | $cm^{-1}$ | C=16.8± 1 | |
| | 5.43 A° | 1375 | $cm^{-1}$ | H= 3.2± .4 | |
| | 6.27 A° | 1570 | $cm^{-1}$ | Sb=50.3±0.5 | |
| | 3.60 A° | | | | |

As Table 1 shows, X-ray diffraction patterns, infrared spectral data and elemental analysis of the trivalent antimony compound of this invention compared with antimony triacetate and antimony glycoloxide indicate vast differences in structure and composition.

Considerations of elemental anaylisis of the trivalent antimony compound and the relative stiochiometry of the 1,2-diol and trivalent antimony reactant affords a basis for postulation of the structure of the trivalent antimony compound as represented by Formulae 1–4.

The above identified antimony compound does not restrict the scope of this invention however. Homologous antimony compounds wherein $R_1$ comprises anion radicals of higher organic carboxylic acids such as propionic, butyric, hexanoic, octanoic, 2-ethylhexanoic and higher and mixtures thereof are within the scope of this invention. In addition, other 1,2-diols may also be employed in place of ethylene glycol as for example 1,2- alkane diols substituted with alkyl groups such as 1,2-propane diol, 1,2-butane diol or 1,2-alkane diols substituted with alkyl halides, such as 3-chloro-1, 2-propane diol. The 1,2-diol can be substituted with many other radicals including sulfur-containing, nitrogen-containing or oxygen-containing radicals and may also be cycloalkane diols such as 1,2-cyclohexane diol or aromatic diols such as orthohydroxy phenol.

In preparing the trivalent antimony compound the 1,2-diol and antimony reactant are combined with stirring to form a viscous reaction mixture. The amount of diol used must be at least one molar with respect to the amount of antimony reactant. Preferably, an excess of diol is used to insure complete reaction. The reaction mixture is heated to between 40°C and 120°C and preferably between 60° and 100°C. Temperatures above 120°C for extended periods of time should be avoided since no appreciable gain reaction rate is achieved. There is also the added danger of decomposing the antimony compound or antimony reactant at elevated temperatures. If alcoholic solvents are employed in the reaction at high temperatures, esters may be formed by the reaction of the alcohols with the organic carboxylic acid replaced in the antimony reactant. The time preferred to complete the reaction varies with the temperatures employed. However, at temperatures between 60° and 100°C the reaction is completed in 15 to 20 minutes. Reaction times greater than 1 hour at high temperatures should be avoided.

A solvent is preferably employed in this process as hereinbefore mentioned. These solvents provide a fluid medium for the reaction and aid in the recovery of the trivalent antimony compound because the antimony compound is insoluble in these solvents and it precipitates therefrom as it is formed. The amount of solvent is not critical but should be added in an amount to insure efficient mixing of the reactants. Usually from 2 g to 3 g of solvent is added for each gram of 1,2-diol.

Antimony glycoloxide, $Sb_2(O-CH_2CH_2-O)_3$ can be produced by treating a trivalent antimony compound of this invention wherein the 1,2-diol dianion radical is ethylene glycol dianion radical with ½ molar equivalents or more of ethylene glycol at high temperatures (80°C or above) for periods of time in excess of 1 hour.

The trivalent antimony compound can be recovered as for example by filtration or centrifugation of the reaction mixture followed by solvent removal and drying of the product. If no solvent is utilized during the reaction, it can be added after the reaction is completed to aid in the recovery of the product as described below.

The antimony reactants can be prepared by methods known in the art. For example, antimony triacetate is generally prepared by reacting antimony trioxide with acetic anhydride at temperatures sufficient to cause reaction. Other antimony reactants such as wherein $R_2$ comprises anions of alcoholates having from 1 to 10 carbon atoms can be produced by reacting one mole of a carboxylic acid with an antimony trialkoxide wherein the alkoxide portion is the same as $R_2$ desired in the antimony starting material. Mixtures of alcoholate anion and anion of organic carboxylic acid can be formed by reacting an appropriate antimony trialkoxide with mixtures of organic carboxylic acids.

Alcoholate anion radicals for $R_2$ having from 1 to about 10 carbon atoms are preferred to give optimum results in yield and rate of reaction. Alcoholate anion radicals having greater than 10 carbon atoms are less desirable to employ in the antimony reactant since they become increasingly more difficult to replace by the 1,2-diol as the number of carbon atoms increase It is preferred to use antimony reactants wherein the organic carboxylic acid anion, $R_1$, contains from 1 to about 10 carbon atoms. Higher organic carboxylic acid anions although useful in this invention are replaced less easily by the 1,2-diol than the carboxylic acid anion radicals containing from 1 to 10 carbon atoms.

In order to more fully describe the instant invention the following examples are given;

EXAMPLE 1

This example illustrates a laboratory preparation of the trivalent antimony compound using antimony triacetate as the trivalent antimony reactant and ethylene glycol as the 1,2-alkane diol. Methyl ethyl ketone was employed as a solvent.

To a 500 ml. reaction flask equipped with stirrer, thermometer and reflux condensor was added 105.8 g. (0.354 m) of antimony triacetate, 28 g. (0.452 m) of ethylene glycol and 77 g. of methyl ethyl ketone.

The mixture was heated to (97°C) under a stream of nitrogen for 15 minutes. The mixture was cooled and then filtered through a Buchner funnel and dried in a vacuum oven at room temperature. The trivalent antimony compound after drying weighed 78.6 g. Yield was 92%. The X-ray diffraction pattern and infra-red spectra were consistent with those given Table 1.

Elemental analysis: Observed C; 16.8±1% H; 3.4±0.4 Sb; 50.3±0.5. The compound had the following solubilities in ethylene glycol at 40°C, 60°C and 80°C;

| Temperature °C | Sb Solubility (g/100) | Compound Solubility (g/100) |
|---|---|---|
| 40 | 1.3 – 1.8 | 2.5 – 3.7 |
| 60 | 3.5 – 3.9 | 6.9 – 7.8 |
| 80 | 5.1 – 5.6 | 10 – 11.2* |

*After prolonged standing (2 weeks) a small amount of solid precipitated which was antimony glycoloxide, $Sb_2(O-CH_2-CH_2-O)_3$.

EXAMPLE 2

This example illustrates a large-scale pilot plant production of the trivalent antimony compound employing methanol as a solvent.

To a 50 gallon Pfaudler reactor was added 185 lbs. of antimony triacetate, 70 lbs. of ethylene glycol and 151 lbs. of methanol. The mixture was stirred and heated at 72°–75°C for 20 minutes under a nitrogen blanket. The reaction mixture was cooled to room temperature and centrifuged through a Sharples centrifuge and the supernatant liquid removed. Analysis of this product was substantially the same as in Example 1. When this product was treated with 2 molar equivalents of ethylene glycol at 80°C for 1 hour, antimony glycoloxide was produced.

EXAMPLE 3

This example illustrates the preparation of a trivalent antimony compound formed by reacting ethylene glycol with a trivalent antimony reactant represented by the formula;

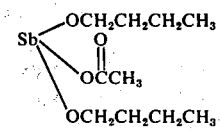

A 50 ml. reaction flask equipped with stirrer, thermometer and reflux condensor was charged with 17 g. (0.05 m) of antimony tributoxide, $Sb(O(CH_2)_3CH_3$. To this was added 3.0 g (0.05 m) of acetic acid. Next, 3.1 g (0.05 m) of ethylene glycol was added to the flask together with 30.0 g of methyl ethyl ketone. The mixture was heated to reflux (90°C) for 15 minutes under a stream of nitrogen. The mixture was cooled to room temperature and filtered through a Buchner funnel. The recovered product was then dried in a vacuum oven at room temperature. The trivalent antimony compound after drying weighed 13.2 g. The infra-red spectrum taken of the product was consistent with the spectrum given in Table 1. When this product was treated with 2 molar equivalents of ethylene glycol at 80°C for 1 hour, antimony glycoloxide was produced.

EXAMPLE 4

This example illustrates the preparation of a trivalent antimony compound comprising a mixed antimony ethylene glycolate and butyrate made by reacting ethylene glycol with antimony tributyrate.

To a 250 ml reaction flask was charged 25.6 g (.067 m) of antimony tributyrate, $Sb(O_2C(CH_2)_2CH_3)_3$. To this was added 19.24 g (0.31 m) of ethylene glycol followed by 70 ml of methyl ethyl ketone. The mixture was heated to 90°C for 15 minutes under a stream of nitrogen and then cooled to room temperature. The infra-red spectrum of the dried product was similar to the infra-red pattern of Examples 1, 2 and 3 except that a more intense peak at 1375 cm -1 was present indicating increased —(CH$_2$)— groupings.

EXAMPLE 5

This example illustrates the preparation of a trivalent antimony compound made by reacting ethylene glycol with an antimony reactant represented by the formula;

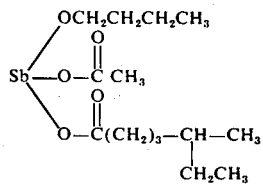

To a 100 ml reaction flask was charged 17.0 g (0.05 m) of antimony tributoxide. To this was added 3.0 g of acetic acid and 7.2 g of 2-ethyl hexanoic acid and heated under vacuum to form the antimony reactant. To this antimony reactant was added 3.1 g (0.05 m) of ethylene glycol and 35.0 ml of methyl ethyl ketone. The mixture was refluxed at 94°C for 15 minutes after which the slurry was cooled, filtered and dried. The infra-red spectrum was similar to those obtained in Examples 1, 2 and 3.

EXAMPLE 6

This example illustrates the preparation of a trivalent antimony compound containing a substituted 1,2-alkane diol dianion radical and acetate anion radical. The 1,2-alkane diol used was 3-chloro-1,2-propane diol.

The procedure of Example 1 was followed except 300 ml of methyl ethyl ketone and 22.0 g (0.2 m) of 3-chloro-1,2-propane diol was added to 0.1 mole antimony triacetate reactant instead of ethylene glycol. After working up the product it was found that the needle like crystals had the following analysis:

| Elemental Analysis | (wt. %) |
|---|---|
| Sb | 41.04 |
| C | 12.72 |
| Major Infra-Red Peaks | |
| 1708cm$^{-1}$ and 1365cm$^{-1}$ | |

EXAMPLE 7

Preparation of polyethylene terephthalate. Exactly 100 g of dimethyl terepthalate, 750 g of ethylene glycol and 0.9 g of zinc acetate dihydrate were heated to a temperature of 190°C under an atmosphere of nitrogen. The reaction was continued for 3 hours collecting 297 g of methanol. This intermediate (100 g) was added to a 200 ml stainless steel flask containing the trivalent antimony catalyst of Example 1 in an amount sufficient to provide 0.025 g atoms of antimony. The temperature was raised to 280°–290°C under a pressure of 0.15 mm Hg. The material was heated for 3 hours under these conditions and the polymer recovered.

What is claimed is:

1. In the process for preparing polyethylene terephthalate from terephthalic acid derivatives and ethylene glycol in the presence of an antimony catalyst, the improvement which comprises using as said catalyst, a trivalent antimony compound having the valences of antimony occupied by dianion radical of a 1,2-alkane diol and organic carboxylate anion radical, said carboxylate anion radical containing from 1 to 10 carbon atoms, wherein the mol ratio of antimony to dianion radical of 1,2-diol to organic carboxylate anion radical is 1:1:1., and wherein said dianion radical of a 1,2-alkane diol is selected from the group consisting of ethylene glycol dianion, 1,2-propane diol dianion, 3-chloro-1,2-propane diol dianion, 1,2-butane diol dianion, and mixtures thereof.

* * * * *